United States Patent [19]

Shaffer et al.

[11] 4,344,712
[45] Aug. 17, 1982

[54] CULTURE PROCESSING APPARATUS AND METHOD

[75] Inventors: Steven D. Shaffer, Chino; L. Michael Kienitz, Riverside; James N. Pitts, Jr., Corona; Richard D. Bliss, Beaumont, all of Calif.

[73] Assignee: The Regents of the University of California, Berkeley, Calif.

[21] Appl. No.: 181,074

[22] Filed: Aug. 25, 1980

[51] Int. Cl.³ .............................................. B01F 11/00
[52] U.S. Cl. ....................................... 366/108; 422/99
[58] Field of Search .............. 366/110, 111, 112, 108, 366/109, 116; 422/99, 102; 134/184

[56] References Cited

U.S. PATENT DOCUMENTS

| 3,289,610 | 12/1966 | Lounsbury | 366/109 |
| 3,295,667 | 1/1967 | Kittle | 366/109 |
| 3,310,292 | 3/1967 | Moore | 366/111 |
| 3,604,689 | 9/1971 | Hutcheson | 366/109 |
| 4,264,559 | 4/1981 | Price | 422/99 |

Primary Examiner—Robert W. Jenkins

Attorney, Agent, or Firm—Herzig & Walsh, Inc.

[57] ABSTRACT

Test apparatus for microbiological cultures includes a vibrating member for placement thereupon of a vessel, such as a petri dish, containing a microbiological culture medium in the form of a liquid film, whereby vibration of the vessel will tend to equalize the thickness of a film formed by solidification of the medium, thereby promoting accuracy of test results. The apparatus further includes a table for placement thereupon of a plurality of vessels containing cultures, the table having a plurality of guides for use in accommodating vessels after removal from the vibrating members. Ramps are disposed on the table adjacent the vibrating members to guide the vessels to the desired position on the vibrating members and to elevate the covers of the vessels so that vibration can occur in a vertical as well as horizontal mode, thereby fostering the desired equalization of the thickness of the culture film in the vessel. A method for obtaining a layer of substantially uniform thickness from a liquid material includes the step of subjecting the liquid material to vibration during solidification.

12 Claims, 5 Drawing Figures

CULTURE PROCESSING APPARATUS AND METHOD

The Government has rights in this invention pursuant to Grant No. PFR7801004A01 awarded by the National Science Foundation.

BACKGROUND OF THE INVENTION

1. Field of the Invention

The invention pertains to apparatus for use in providing thin, substantially uniformly thick layers of material and, in particular, in connection with testing and study of microbiological cultures.

2. Description of the Prior Art

Testing and study of microbiological phenomena are, of course, extremely widespread and have applications in extremely varied fields of endeavor. Of increasing importance has been the application of microbiological techniques to testing of chemicals and environmental pollutants. It has been discovered that there is a very strong correlation between the tendency of a particular chemical to cause genetic mutations in bacteria ("mutagenicity") and the ability of such chemical to cause cancer ("carcinogenicity") in mammals and man. A particular application of this corporation is in the "Ames *Salmonella/mammalian*" microsome mutagencity test.

In the Ames test, test micro-organisms consist of bacteria mutated so that they are unable to synthesize histidine, an amino acid required for growth. The test bacteria are placed in a culture lacking histidine and including a chemical to be tested. If the chemical is not mutagenic, then the test bacteria will not be able to grow in the histidine-free culture; however, if there are mutagenic materials present, they will promote a reversal of the original mutation (which disabled the bacteria in the first place from synthesizing histidine); the test bacteria experiencing such a reversal (referred to as a reversion) will grow and form visible colonies. Thus, the appearance of colonies indicates that the chemical under test is mutagenic and probably carcinogenic as well. The degree of mutagenicity is determinable from the number of colonies produced by a given amount of the material under test.

Normally, the bacterial culture is continued in a vessel known as a petri dish comprising a covered container. The test compound contains besides the test material and the test bacteria a gelling agent. The mixture, in liquid form, is heated to melt the gelling agent and is then poured into the vessel, over a solid gelling agent, thus forming a thin film which solidifies upon cooling.

It is extremely desirable that the film containing the culture medium be of uniform thickness, which facilitates electronic counting of bacterial colonies, indicating the degree of mutagenicity. Inaccuracy results with such electronic counters if the thickness of the film in the culture medium is uneven in the petri dish. Also desirable is a capability of processing samples in batches as opposed to singly, thus facilitating efficiency.

In existing methods, spreading of the medium accomplished manually, with obvious drawbacks. Also, in existing methods and apparatus, processing of samples is usually on an individual as opposed to a batch basis. The device depicted and described in U.S. Pat. No. 3,310,292 issued Mar. 21, 1967, for "Serological Testing Device" utilizes vibration for agitating components in serological testing. Such device, however, does not function to equalize thickness of a layer of a compound and provides only for a limited number of items in a batch of samples to be processed simultaneously and requires individual lowering and lifting of slides used in connection with testing.

Thus, there has been a felt but unfulfilled need for apparatus for providing a thin, substantially uniformly thick layer of material, for testing and other purposes, and having the capability of conveniently processing a plurality of items simultaneously.

SUMMARY OF THE INVENTION

Apparatus for providing a solid layer of substantially uniform thickness from liquid material in a vessel having a cover comprises a vibrator member for placing a vessel having a movable cover and containing liquid material for forming a solid layer of substantially uniform thickness, in contact therewith, and means connected with the vibrator member for lifting the cover of the vessel during placement of the vessel in contact with the vibrator member in order to permit vibration of the vessel in a substantially vertical direction. A support structure has the capability of supporting a plurality of vessels after vibration thereof. The support structure and vibrator member are positioned so that vessels can be slid therebetween.

A method in accordance with the invention comprises placing liquid material in contact vibrator means during solidification of the liquid material so that a solid layer of substantially uniform thickness is provided upon solidification of the liquid material.

DETAILED DESCRIPTION OF THE INVENTION

Figure 1:
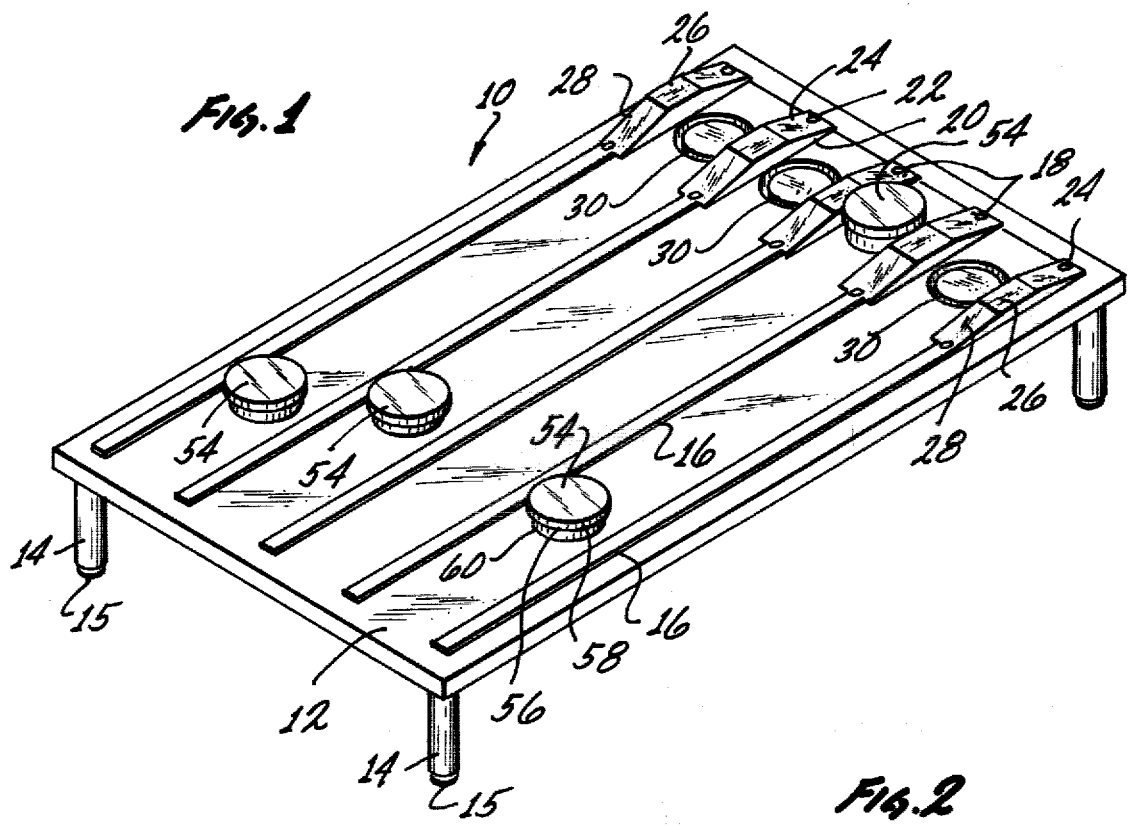
FIG. 1 is a perspective view of apparatus in accordance with the invention.

As depicted in FIGS. 1 through 4, inclusive, apparatus 10 in accordance with the invention includes a table 12 supported by legs 14 having feet 15 which are adjustable to level table 12. A plurality of guide members 16 are disposed at the upper surface of the table 12. Members 16 comprise tracks which are slightly elevated from the surface of the table 12 and extend longitudinally along the upper surface of the table 12 from adjacent one end thereof. At the other end of each member 16 is a ramp member 18. In the embodiment depicted, members 16 are five in number. Members 16 and their respective ramps 18 thus form four spaced-apart pairs.

Ramps 18 include a base section 20 resting upon the surface of table 12. An elevated section 22 of ramp 18 is configured to comprise a first incline 24 extending from the end of track guide 16 to a level region 26. Level region 26 extends from the first incline 24 to a second incline 28, which is disposed symmetrically with respect to the first incline 24. Elevated section 22 of the ramp is fastened to the base section 22 by pairs of ears 30 frictionally engaging the base. A support block 32 is disposed between the base section 20 and the ramp 22 for support of the ramp. Screws 33 fasten each ramp 18 to the table 14.

A vibrating member 34 is disposed between each pair of ramps 18. The vibrating member 34 is generally cylindrical in form and includes a vibrator platform 36. Platform 36 is substantially flush with the table 12 and is supported upon vibrator means which may comprise any appropriate vibrating means, such as a cone 38 of a speaker 40 as depicted herein. Other vibrating means may, of course, be utilized in accordance with the invention. Speaker 40 is contained in a housing 41 having lateral walls 42 and a connector 44. Connector 44 is connected to table 12 by screws 45 on which are disposed coil springs 46. Screws 45 are adjustable to level the speaker 34 for maximum effectiveness. Power to individual speakers is controlled by attenuator pads 48 disposed within speaker housing 41. The speakers are driven by adjustable electronic oscillators and amplifiers (not shown) contained in a driver housing 58 connected to speaker housing 42.

Figure 2:
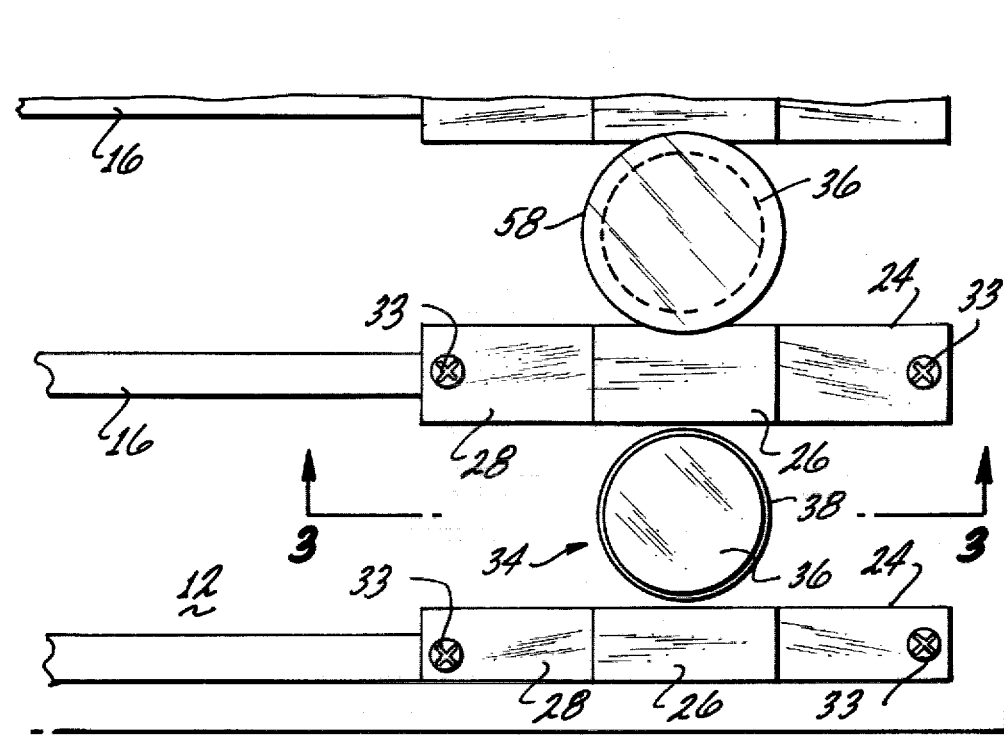
FIG. 2 is a fragmentary view of a portion of the top of apparatus depicted in FIG. 1.
Figure 3:
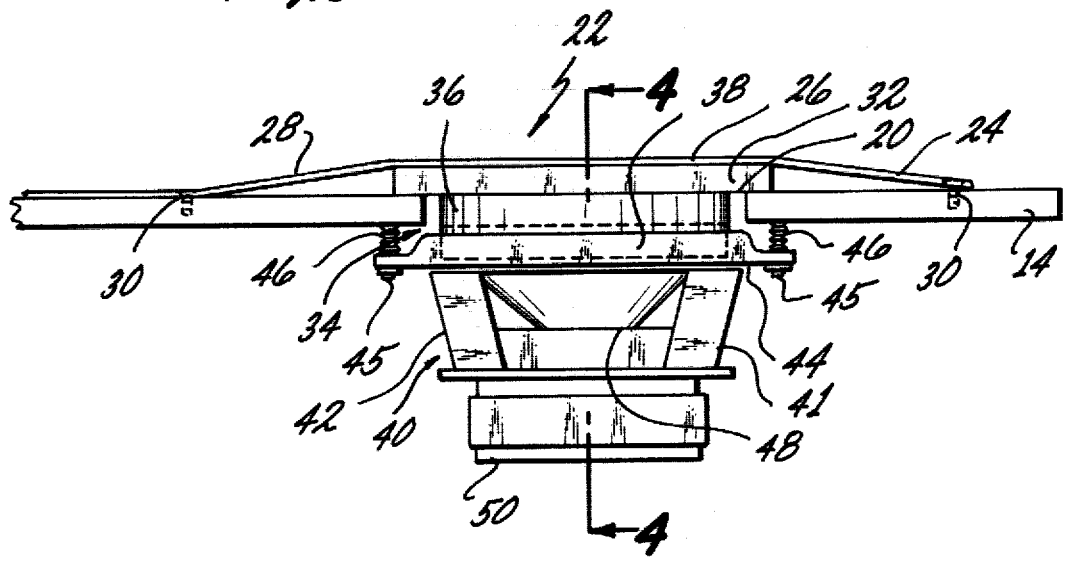
FIG. 3 is a sectional view, partially broken away, through the line 3—3 of apparatus in accordance with the invention.
Figure 4:
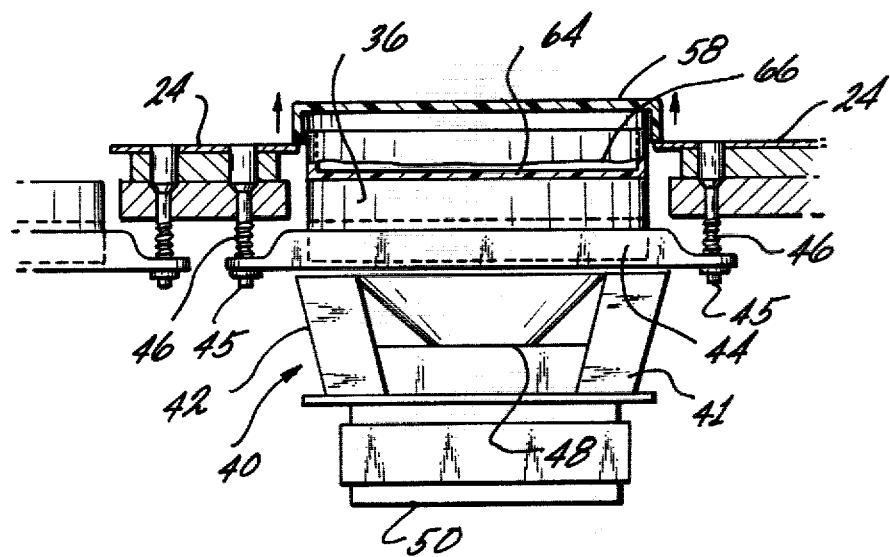
FIG. 4 is a sectional view, partially broken away, along the line 4—4, of apparatus in accordance with the invention.

As best seen in FIGS. 1, 2 and 4, vessels in the form of petri dishes 54 are disposed on table 12. Other vessels may, of course, be employed in accordance with the invention. Each petri dish 54 includes a bowl-like container 56 and a flanged cover 58 disposed over container 56. The flanged cover 58 fits over the bowl 56 so that the flange of the cover extends downwardly along the walls 60 of the container 56.

In operation, a culture or other material to be tested or investigated is prepared in liquid form and placed in the container 56 portion of petri dishes 54. In a specific example comprising the Ames *Salmonella/mammalian* microsome mutagenicity test, a culture medium of the bacteria to be tested is prepared by mixing a liquid sample of the compound to be tested with the test bacteria, together with a small amount of liquid gelling agent, such as agar, which is at a slightly elevated temperature. The mixture is then poured over a substrate 64 (depicted in FIG. 4) of solid agar at the bottom of the petri dish 54; a thin layer of liquid 66 (depicted in exaggerated size in size in FIG. 4) is then present upon the agar substrate 64.

The petri dish 54 is then placed upon table 12 and slid between ramps 18 onto speaker platform 36 in contact with outer incline 24 of each ramp 18. The flanged cover 58 of petri dish 54 is slightly wider than the container portion 60 of the petri dish (FIG. 2), the the ramps are spaced apart so that the bottom edges of the flanged cover 58 of the petri dish 54 will be in contact with the upper surface of the inclines 24 of the ramps 18. As a result of the contact between the inclines 24 and the cover 58 of the petri dish 54 in connection with motion of the petri dish 54 toward the speaker platform 36, the ramps exert a camming effect so that the cover 58 of the petri dish is moved slightly in the vertical direction with respect to the container 56 of the petri dish. Thus, when the petri dish reaches the platform 30, the cover 58 is resting upon flap portion of the ramps 18 and is slightly elevated above the container 56. The petri dish and the contents thereof are then subject to vibration of the speaker platform 36. Such vibration may have a duration of approximately one minute or such other selected time as is appropriate for the particular application. Vibration amplitude may be selected as desired. Because of the elevation of the cover 58 from the dish 54, the latter is free to vibrate in the vertical direction.

As a result of vibration of the liquid culture medium, the solid film of culture medium which forms upon cooling is of substantially uniform thickness. Such uniformity promotes and facilitates accuracy of test results. This is applicable to the particular example given, namely, the Ames *Salmonella/mammalian* microsome mutagenicity test, as well as to other scientific and industrial applications in which uniformity of thin films formed from liquid material is of importance.

Following the prescribed period of vibration, the petri dish containing the culture medium under study is slid in the same direction as it was moved from the end of the table 12 onto the platform member, thus causing contact of the underside of the cover 58 of the petri dish 54 along the inclines 28. Contact of the petri dish cover 58 with the inclines 28 in connection with sliding the petri dish 54 off the platform member 30 causes the cover 58 to resume its former position of resting upon the top of the container 56 of the petri dish 54. At this point, the dish 54 is disposed between track guides 16 and may be left on the table or removed. In a particular mode of operational use of the table, a batch of petri dishes can be vibrated simultaneously, and at the expiration of the prescribed duration of vibration will be displaced from the platform member by the sliding of a second batch of petri dishes onto the platforms for vibration. In this manner, efficient placement on, and removal, from, the platforms 36 can be effected. The table 12 is configured so that a number of batches can be processed in this manner with petri dishes from previously vibrated batches remaining on the table until it is deemed desirable to remove them.

Figure 5:
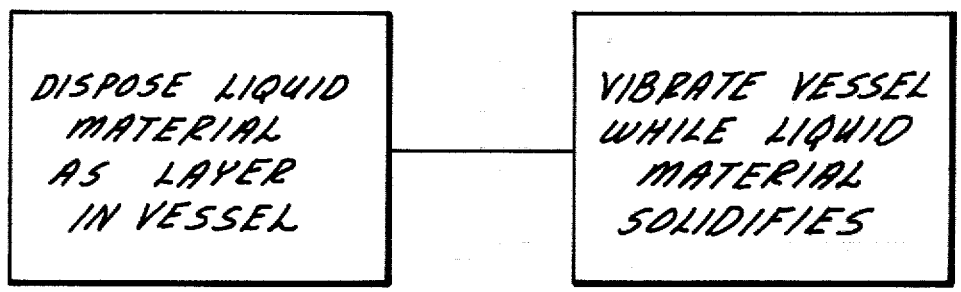
FIG. 5 illustrates in schematic form a method in accordance with the invention.

As depicted in FIG. 5, a method in accordance with the invention comprises the steps of placing a layer of liquid material to be solidified into a solid layer into a vessel and vibrating the vessel during solidification of the liquid, to achieve a desired substantially uniform thickness of the solidified layer of material.

Although a particular embodiment of the invention has been described and depicted hereinabove, the invention is defined solely in terms of the appended claims interpreted in light of the specification.

What is claimed is:

1. Apparatus for providing a solid layer of substantially uniform thickness from liquid material in a covered vessel comprising:
    a vibrator member for placing a vessel having a movable cover and containing liquid material for forming a solid layer of substantially uniform thickness, in contact therewith; and
    means connected with said vibrator member for lifting the cover of said vessel during placement of said vessel in contact with said vibrator member, to permit vibration of the vessel in a substantially vertical direction.

2. The invention as set forth in claim 1 further including a support structure for supporting at least one said vessel, wherein said vibrator member is positioned such that said vessel can be moved along said support structure and into contact with said vibrator.

3. The invention as set forth in claim 2 wherein said means for raising the cover of said vessel comprises at least one pair of ramp members and wherein said vibrator member is disposed between said pair of ramp members, the latter including inclined sections for contacting the underside of said cover and for raising said cover in connection with moving said vessel into contact with said vibrator member.

4. The invention as set forth in claim 3 wherein said support structure comprises a table and wherein said vibrator member includes a platform member substantially flush with the top surface of said table such that said vessel can be moved along said table into contact with said platform member.

5. The invention as set forth in claim 4 further including a plurality of pairs of ramp members and a plurality of platform members such that one platform member is disposed between each pair of ramp members and wherein each said ramp member includes a second incline other than the first-mentioned incline, such that when said vessel is moved away from said vibrator member in the same direction as it was moved onto the vibrator member, the cover of said vessel contacts said incline thereby being lowered to its original position with respect to the vessel.

6. Apparatus for providing a layer of substantially uniform thickness formed from liquid material in a vessel comprising:
   a table member;
   a vibrator member for vibrating said vessel by contact therewith and being disposed on said table so that said vessel can be moved along said table into contact with said vibrator member;
   at least one pair of ramp members disposed adjacent said vibrator member and configured to define incline means for contacting said cover of said vessel such that upon motion of said cover onto said vibrator member, said cover will be lifted.

7. The invention as set forth in claim 6 wherein said ramp member includes an incline, other than the first-mentioned incline, for contacting said cover of said vessel such that upon motion of said vessel away from said vibrator member in the same direction as said vessel was moved into contact with said vibrator member, said cover is lowered to its original position on said vessel.

8. The invention as set forth in claim 7 wherein said at least one pair of ramp members is positioned on said table member such that when a vessel is moved away from said vibrator member in the same direction as it was moved onto the vibrator member, said vessel will rest upon said table member.

9. The invention as set forth in claim 8 wherein said table member includes at least one pair of spaced-apart track guide members, each said track guide member extending above said table member and being disposed along said table member and having one end at one of said ramp members, said guide track members being spaced apart to accommodate at least one vessel moved away from said vibrator member.

10. The invention as set forth in claim 6 wherein said vibrator member is substantially flush with the surface of the table member.

11. The invention as set forth in claim 10 wherein said vibrator means comprises speaker means.

12. The invention as set forth in claim 11 wherein said speaker means is attached to said table member by means which are adjustable to level said vibrator member.

* * * * *